United States Patent [19]

Elias et al.

[11] Patent Number: 4,618,937
[45] Date of Patent: Oct. 21, 1986

[54] SPOT QUANTITATION

[75] Inventors: John G. Elias, Wilmington; Peter A. Jansson, Hockessin, both of Del.

[73] Assignee: E. I. Du Pont de Nemours and Co., Inc., Wilmington, Del.

[21] Appl. No.: 574,713

[22] Filed: Jan. 27, 1984

[51] Int. Cl.[4] .................... G06F 15/20; G06K 9/00
[52] U.S. Cl. .................... 364/518; 364/570; 364/525; 364/415; 382/6
[58] Field of Search ............ 364/555, 521, 523, 525, 364/570, 413, 415, 416, 518; 382/6

[56] References Cited

U.S. PATENT DOCUMENTS

| | | | |
|---|---|---|---|
| 3,908,078 | 9/1975 | Auerbach et al. | 364/415 X |
| 4,192,004 | 3/1980 | Buerger | 364/518 X |
| 4,267,573 | 5/1981 | Chaikin et al. | 364/518 X |
| 4,404,683 | 9/1983 | Kobayashi et al. | 364/416 X |
| 4,450,530 | 5/1984 | Llinas et al. | 364/413 X |
| 4,455,609 | 6/1984 | Inamura et al. | 364/413 X |
| 4,481,509 | 11/1984 | Sasaki et al. | 364/518 X |
| 4,485,411 | 11/1984 | Yamamoto | 364/518 X |
| 4,522,482 | 6/1985 | Pettigrew et al. | 364/518 X |

OTHER PUBLICATIONS

"Quantitation of Brain Proteins by Computer-Analyzed Two Dimensional Electrophoresis" in Catsimpoolar, N., (Ed.), Electrophoresis, 1978, Lutin, W. A., Kyle, C. F. and Freeman, J. A.

"Implementation and Application of a Method to Quantitate 2-D Electrophoresis Patterns", 1983, 4, pp. 82-9-1—Jansson, P. A., Grim, L. B.; Elias, J. G.; Bagley, E. A. and Lonberg-Holm, K. K.

Primary Examiner—Edward J. Wise

[57] ABSTRACT

Describes a method and system for improving the ability to quantitate the amount of flux or material in localized collections of such flux or material typically called a "spot". Quantitation of spots using a software algorithm which utilizes models in two opposite senses for quantitating peaks in a spot image of an electrophoresis gel is disclosed. The operating system includes a laser gel scanner module, a computer module, system peripherals, and analysis software.

11 Claims, 8 Drawing Figures

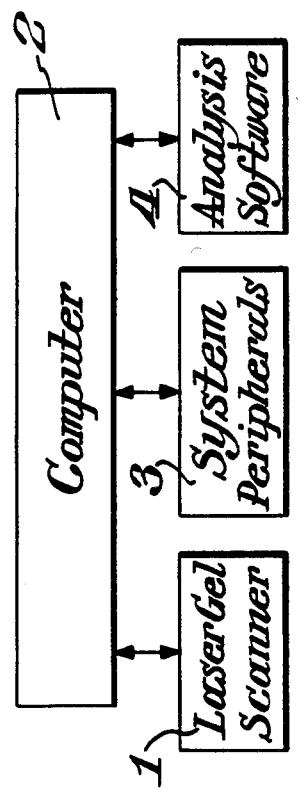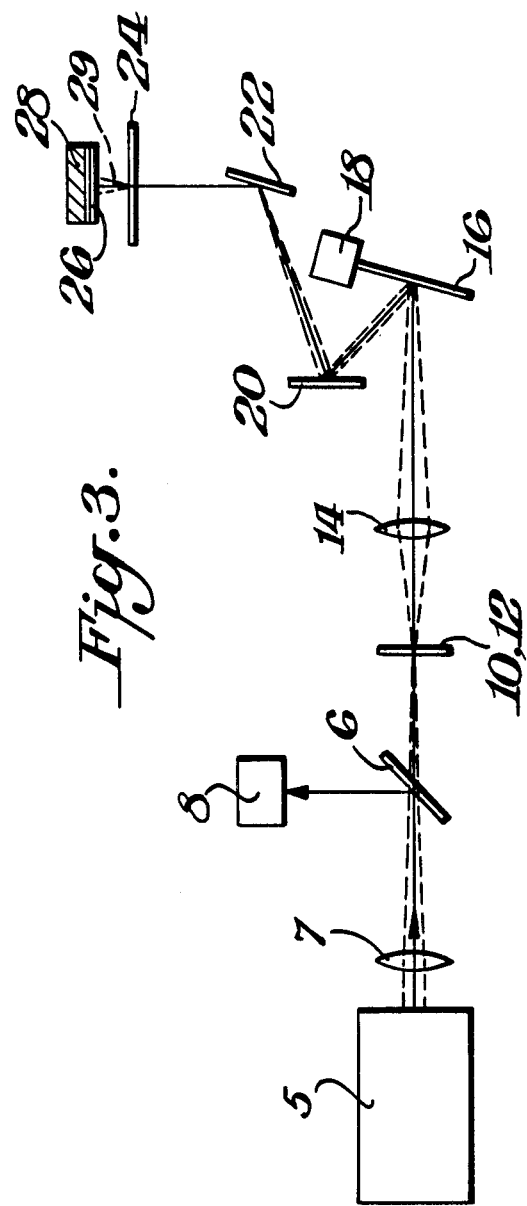

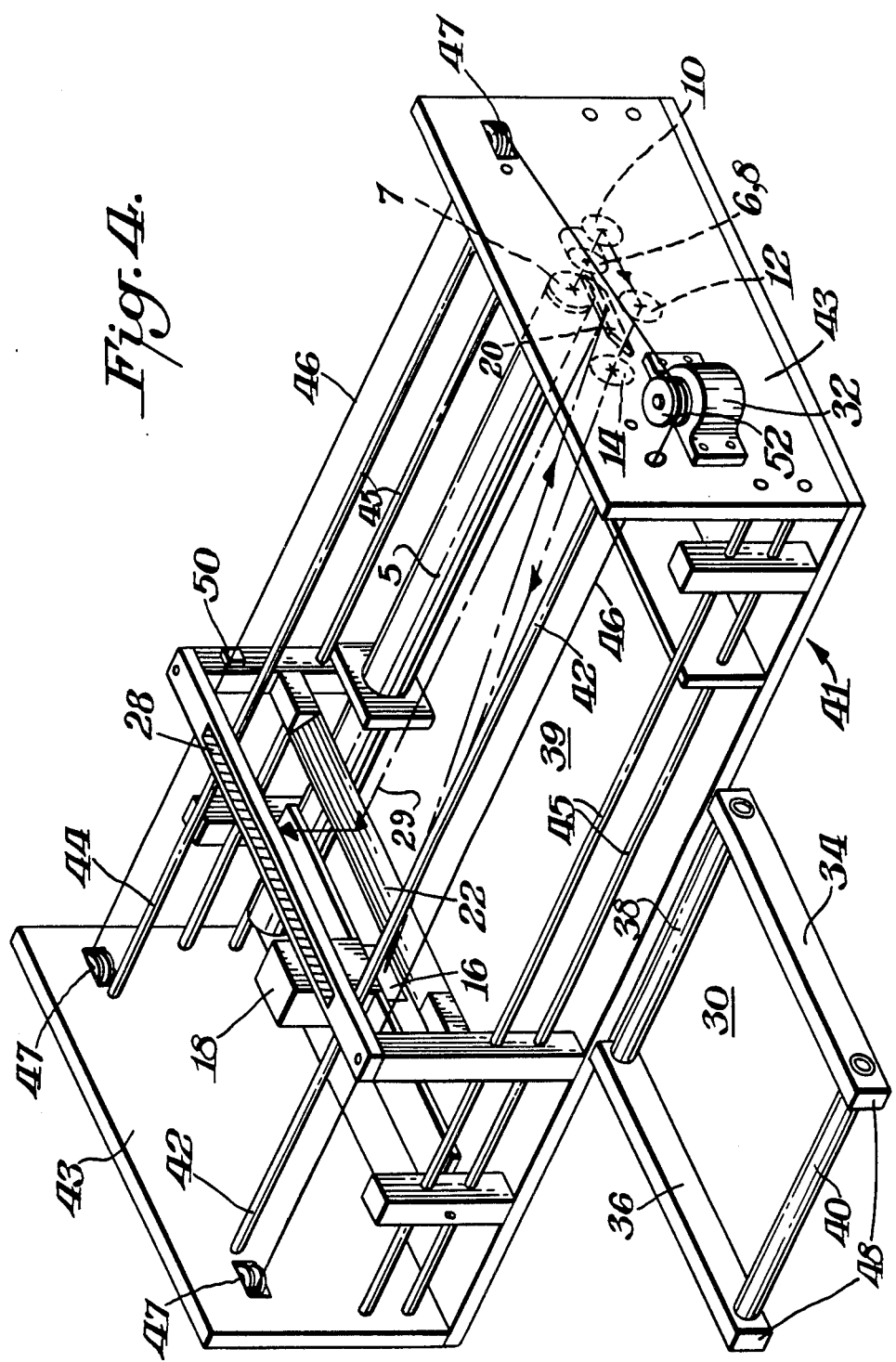

Fig. 7.

IMAGE

| Row Number | Column Number | | | | | | | |
|---|---|---|---|---|---|---|---|---|
| | 1 | 2 | 3 | 4 | 5 | 6 | 7 | 8 |
| 1 | 1 | 1 | 1 | 2 | 3 | 5 | 1 | 1 |
| 2 | 1 | 1 | 3 | 5 | 6 | 7 | 5 | 2 |
| 3 | 1 | 2 | 3 | 5 | 6 | 4 | 2 | 1 |
| 4 | 1 | 2 | 2 | 3 | 4 | 3 | 2 | 1 |
| 5 | 1 | 3 | 4 | 3 | 2 | 2 | 1 | 1 |
| 6 | 1 | 3 | 7 | 5 | 3 | 1 | 1 | 0 |
| 7 | 0 | 1 | 4 | 3 | 2 | 1 | 1 | 0 |
| 8 | 1 | 1 | 1 | 2 | 1 | 1 | 1 | 0 |

ZMAX TABLE

| Row Number | Maximum | Column Location of Maximum |
|---|---|---|
| 1 | 5 | 6 |
| 2 | 7 | 6 |
| 3 | 6 | 5 |
| 4 | 4 | 5 |
| 5 | 4 | 3 |
| 6 | 7 | 3 |
| 7 | 4 | 3 |
| 8 | 2 | 4 |

SPOT QUANTITATION

CROSS REFERENCE TO RELATED PATENT APPLICATIONS

The invention described herein relates to an invention described in copending application entitled Spot Quantitation, Ser. No. 574,712, filed Jan. 27, 1984, by Elias et al.

BACKGROUND OF THE INVENTION

This invention relates to a method and system for improving the ability to quantitate the amount of flux or material in localized collections of such flux or material typically called a "spot". These spots, encountered in such fields as astronomy, chemistry, biology, and the like, may be distributed in patterns, constellations or other configurations. The problems are essentially the same in all of these fields-each spot must be located, resolved from possible overlapping spots and quantitated.

In the area of biotechnology, recent advances in separation technology, in particular two-dimensional gel electrophoresis, have made it possible to separate large numbers of different components that may be present in a complex protein mixture. Typically the separation is carried out on the basis of molecular charge in one dimension and molecular weight in the other. Protein spots thus separated may be stained and viewed directly. Scientists have estimated that 30,000 to 50,000 human-protein gene products may exist. In identifying a given protein after electrophoresis-gel separation, the researcher identifies spots of interest by their known placement in the characteristic overall spot pattern. Quantities of protein are typically judged in a subjective fashion that is not quantitatively accurate. Visual analysis of high resolution gels is laborious and time-consuming owing to the large number of spots that may be present, some of them barely visible. It is easy to overlook changes in the pattern that may be important. Furthermore, accurate determination of the amount of protein present in certain spots is necessary for a number of experiments, including longitudinal studies of clinical patients, and the kinetics of blood chemistry.

In order to improve upon the efficiency and precision by which a spot is analyzed, scientists have utilized automated gel quantitation systems incorporating computers to process the spot pattern images. Several analysis methods that have been used with 2-D gels work well with isolated spots, but are unable to accurately allocate protein between two spots that show overlap. Although a number of the spots on a typical gel are relatively free of overlap with neighbors, enough spots show overlap to make resolvability a very important consideration.

A typical gel quantitation system has four principal components: scanner, software, computer and display. A scanner, typically transmissively or reflectively, converts the image into an array of numerical gray level measurements usually termed pixels, each pixel representing an element of the array, suitable for computer manipulation.

The spots or pixels are obtained in several different ways. For example, the proteins to be separated may be radiolabeled. The radiation flux from these proteins after separation may be used to expose photographic film, thereby forming an autoradiogram of the gel. Or, the proteins may be stained by an optically absorbing material after separation. By either method, a pattern of optically absorbing spots is produced that may be measured with the aid of a scanner or scanning densitometer. The output of such a scanner is typically a series of measurements of the optical density of the stained gel or autoradiogram sample, these measurements being regularly spaced in a rectangular array that covers substantially the entire surface of the sample. The software is a collection of computer programs designed to analyze the data supplied by the scanner. The computer analyzes the pixel data by executing the instructions provided by the software. A display system demonstrates the results of this analysis, and permits the user convenient interaction with data and results if necessary.

Many improvements have been made in scanners, computers, and display systems to help quantitate spots, but the area that needs more attention is the quantitation of the spots. A spot can be considered to be a three-dimensional mountain peak with peak height corresponding to maximum spot density, i.e., quantity of protein, surrounded by neighboring peaks of varying width and amplitude. In the prior art there are two general approaches used to quantitate spots. The first approach deals with simple segmentation and contour following; the second approach deals with modeling. Of the two approaches, only modeling can adequately resolve overlapping spots.

A paper by Lutin, W. A., Kyle, C. F. And Freeman, J. A., "Quantitation of Brain Proteins By Computer-Analyzed Two Dimensional Electrophoresis", in Catsimpoolas, N, (Ed.), *Electrophoresis '78*, (Elsevier North Holland, New York 1979), pp. 93–106, describes one such modeling approach. As taught by Lutin et al., the raw scanner data are acquired in the form of pixels or numbers representing the gray level intensity of the spots. These pixels are then processed by the computer to determine which levels of intensity represent the background values. The background pixels are fitted by least squares to a two-dimensional polynominal. The image is then corrected for background variation by subtracting the polynominal value at each pixel location. In addition, the corrected image is smoothed by convolution.

The corrected data now are searched for a maximum value, the tacit assumption being that this value must be at the approximate center of a peak. Once the peak center has been found, inflection points of the peak are sought by scanning the data in all four raster directions away from the maximum found.

The average height of the four inflection points relative to the peak height is compared to that expected for a true gaussian. If a serious discrepancy is noted, the peak is assumed to be subject to interference from a neighboring peak and a Gaussian estimate is made from the inflection point value and maximum values obtained. Inflection points not lying in a plane, or an inflection point plane that is significantly titled, are also indications that an estimate is necessary. If, on the other hand, the inflection points are those expected for a single isolated gaussian, a weighted least-squares Gaussian fit is performed over the two-dimensional region bounded by the inflection points in order to obtain the Gaussian parameters.

The Gaussian parameters, whether obtained by estimation or fitting, are then used to create a gaussian that is subtracted from the surface. The data are searched again for a maximum. The previously found maximum is, of course, no longer present so a new peak is located. This procedure is continued until the maximum found is below a preset threshold level. When this occurs, the first gaussian is regenerated from its parameters, which have been stored in a list. This gaussian is then added to the surface. Inflection points are tested as before, and the gaussian is either fitted or estimated, then subtracted again. This time, however, the gaussian is found to be less influenced by neighboring peaks, the largest ones have already been removed, at least to a good approximation. The fit or estimate is thus more likely to be accurate. By this means, one is able to obtain good fits while treating only one gaussian at a time. The process is repeated for all gaussians already on the parameter list. After the last gaussian is processed, additional image maxima are determined. Additional gaussians are thus found and subtracted until a lower threshold is reached. Three such passes are made through the list. Each time, the threshold is lowered according to a predetermined sequence of values. After the third pass, a fourth and final pass is made in which estimation is not allowed and a least squares fit is forced for all gaussians.

Although this algorithm is an improvement over the prior art, it requires multiple passes to complete the process, each gaussian being treated several times. This excessive computation results in overall loss of efficiency. In addition, the prior art does not address the problem of negative residuals. These negative residuals are a result of subtracting a Gaussian model whose value in places exceeds the value of the data being modeled. The appearance of a negative residual is an indication that the parameters that were estimated or fitted to the actual peak represent a larger volume than is actually present. In other words, the values used to describe the spot (peak) are in error. Other problems with the prior art include numerical failures that occur when the matrix derived from the least-square normal equations becomes ill-conditioned.

An improved approach to quantitating spots is described in a paper by Jansson, P. A., Grim, L. B., Elias, J. G., Bagley, E. A. and Lonberg-Holm, K. K., "Implementation and Application of a Method to Quantitate 2-D Gel Electrophoresis Patterns" *Electrophoresis* 1983, 4, pp. 82–91, in which the analysis achieves greater stability. Jansson, et al., felt that one aspect of the prior art that needed adaptation was the cut-off criterion. This is the pre-determined density at which the algorithm specifies that peak subtraction is to stop, and peak addition, refitting and re-subtraction is to begin. This process is repeated until a new and lower cutoff is reached. Jansson, et al., noted that the arbitrary cutoff previously employed was too high, so that weak spots would be missed. At other times it was too low, so that large numbers of minute gaussians were fitted to noise. The solution to this problem was the introduction of a mathematical expression that specified this cut-off point by referring to known background parameters. This modification, although it yields an improvement in time efficiency, still does not address the problem of negative residuals, which introduce error in the quantitation of a protein spot. Also, this system is still iterative, utilizing multiple passes to treat each gaussian which is, in turn, time-consuming. This time burden can be relieved by the use of large main-frame computers. The use of these computers is, however, undesirable due to expense and lack of convenience.

SUMMARY OF THE INVENTION

This invention directly addresses the problems of accuracy, time efficiency and expense by an improved spot quantitation method and system. According to the method of this invention, spatially integrated intensities of individual spots are quantitated. The spots are contained in a multiple spot image defined by a discrete pixel-by-pixel representation of the intensities of the spots. Quantitation of these spots is accomplished by, (a) searching the image for the pixel representating the greatest intensity deviation in each of the two opposite senses from a reference intensity level, (b) constructing a mathematical three-dimensional model in a sense corresponding to the sense of the maximum pixel found, of the spot containing such pixel, (c) compensating the image by subtracting the mathematical model therefrom leaving possible overcompensated regions in the image, which in turn can give rise to additional pixels that will subsequently be detected in step (a), (d) quantitating the spot from the model, and (e) repeating steps (a) through (d) for successive pixels each having a lower intensity deviation from the reference level until the image is of substantially constant intensity.

The model of step (b) is partially defined by searching the image in four orthogonal directions from the greatest deviation pixel to ascertain the extent of the spot along each direction. Models formed in step (b) of adjacent pixels are combined to form composite models of each individual spot.

The method includes the additional steps of quantitating the spot to obtain its center of mass and moments of inertia, and determining the extent of the model according to the parallel-axis theorem. The method differs from that in the copending application in that reduction volumes are here not employed to correct for overcompensated regions, the required correction being instead effected by the use of models in either of two opposite senses.

The invention is also a system for quantitating individual spots contained in a multiple spot image defined by a discrete pixel-by-pixel representation of the intensity of the spots, the system including a memory for storing the pixels, means for determining that pixel representing the greatest intensity deviation from a reference intensity level, and means for constructing a mathematical three-dimensional model of the spot containing such pixel.

This system is improved in accordance with this invention by means included in the means for determining that pixel representing the greatest intensity deviation in each of two opposite senses from the reference intensity level, means included in the constructing means for constructing the model in a sense corresponding to the sense of the maximum pixel found, and means for compensating the image by subtracting the mathematical model therefrom leaving possible overcompensated regions in the image which in turn can give rise to additional pixels that will subsequently be detected, and means for quantitating the spot from the model.

BRIEF DESCRIPTION OF THE DRAWINGS

The detailed operation of the method and system described briefly above can be best understood by reference to the following drawings in which:

FIG. 1 is a block diagram of a two-dimensional-Gel Analysis instrument constructed in accordance with this invention;

FIG. 3 is a drawing illustrating the laser beam focusing and directing optics used in the gel scanner of FIG. 1;

FIG. 4 is a pictorial illustration of the scanner mechanical assembly;

FIG. 7 illustrates the use of a max table, which enhances the efficiency of the method.

SYMBOLS

Figure 2:
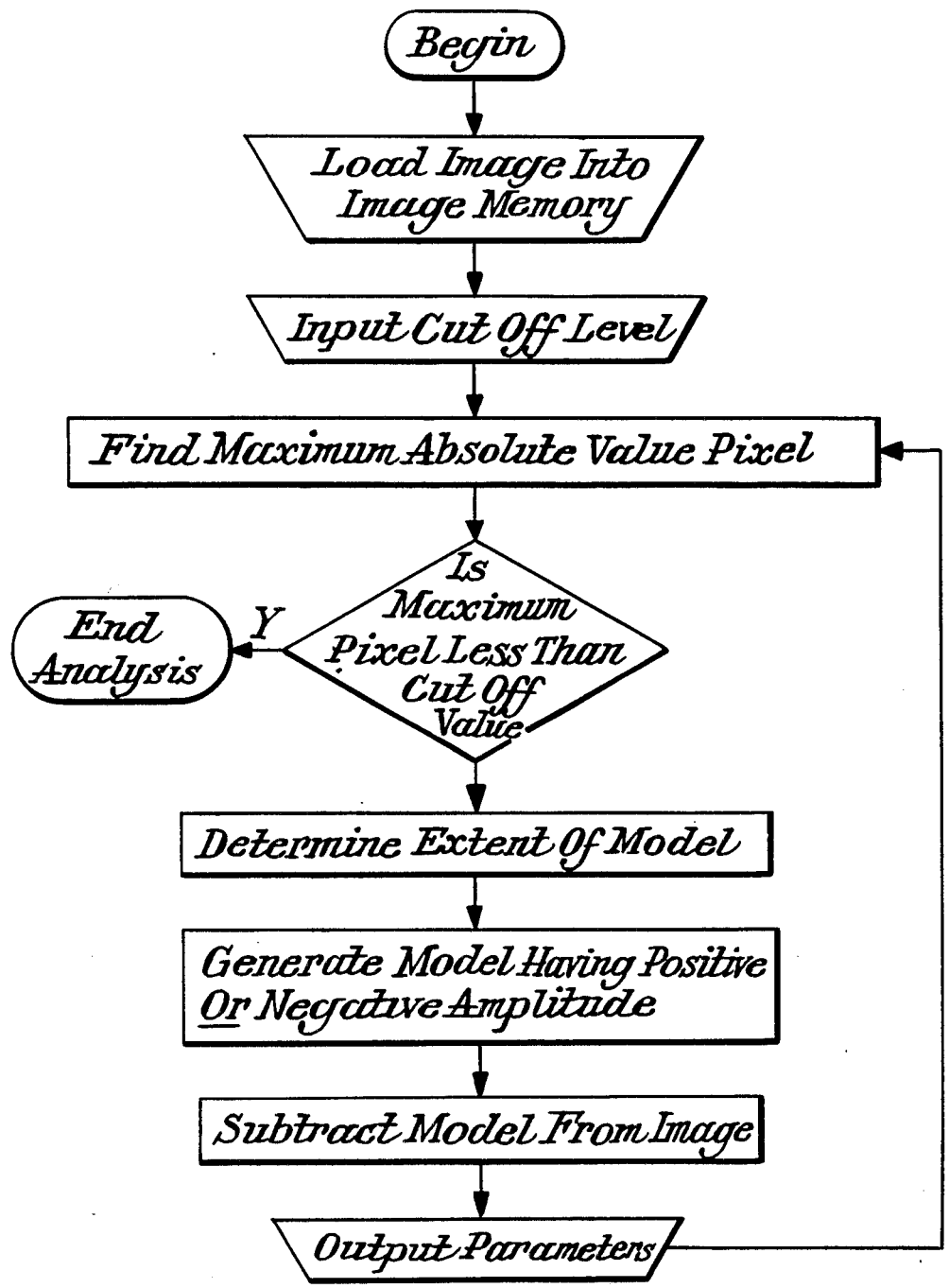
FIG. 2 is a flow diagram describing the manner in which spot patterns are automatically quantitated in accordance with this invention.

The following is a table of symbols that defines the mathematical parameters used throughout the disclosure for convenience of the reader.

$z(x,y)$: Intensity samples of image.
$z_M(x,y)$: Assymetric Gaussian model.
$V$: Volume of model.
$x,y$: Cartesian coordinates in gel image plane.
$x_o, y_o$: Coordinates of center of model; coordinates of maximum pixel.
$A$: Amplitude of Gaussian model; value of maximum pixel.
$\sigma_{x+}, \sigma_{x-}, \sigma_{y+}, \sigma_{y-}$: Principal inflection point distances from the absolute value maximum pixel.
$\bar{x}, \bar{y}$: Cartesian coordinates of the model center of mass.
$\sigma_x^2, \sigma_y^2$: Variances of a 4-component Gaussian model about it's center of mass.
$\bar{V}$: Volume of spot comprising N gaussians.
$\bar{x}_{CM}, \bar{y}_{CM}$: Center of mass of spot comprising N-gaussians
$\bar{\sigma}_x, \bar{\sigma}_y$: Standard deviation of spot comprising N-gaussians.

DETAILED DESCRIPTION OF THE PREFERRED EMBODIMENT

Overview of the System

Referring to FIG. 1, there is seen a system that may be used to quantitate spots used in performing the method of this invention. The system is described in one of its applications, i.e., quantitating the spots of an electrophoresis gel. It is to be understood, however, that the method and system are equally appliable to quantitating other spot patterns as well, i.e., those encountered in astronomy, as well as in chemistry and biology. Although the method and system of this invention relate to the quantitation of the spots in a spot image, in order to provide a complete disclose of an operative system, a gel scanning system that has been successfully built and operated to scan a spot image and provide a pixel-by-pixel representation thereof is described.

The system includes a laser gel scanner module 1, a computer module 2, system peripherals 3, and analysis software 4. The laser gel scanner 1 digitizes, with high resolution, the two-dimensional optical-density information in 2-D electrophoresis gels. The computer system 2 serves many functions. It transmits the scan parameters to the laser scanner's control circuitry. It assists in the transfer of data from the scanner to an image memory. It processes the image data according to specially designed algorithms. And, it helps to effect data movement from various storage systems to a video display device. The system peripherals include a CRT terminal, color monitor, printer and floppy disk drive and hard disk drive.

I. METHOD OF THE INVENTION

The method of this invention, which overcomes many of the difficulties experienced in the prior art, is a "one-pass" method that treats each spot or peak once. After each spot has been modeled and the model subtracted from the image, the resultant model's parameters are stored and not accessed again until it is time to combine the individual resultant models into spot structures. If some of the spots are overcompensated, negative regions, i.e., negative residuals, are modeled in addition to the positive peaks or regions.

Figure 6:
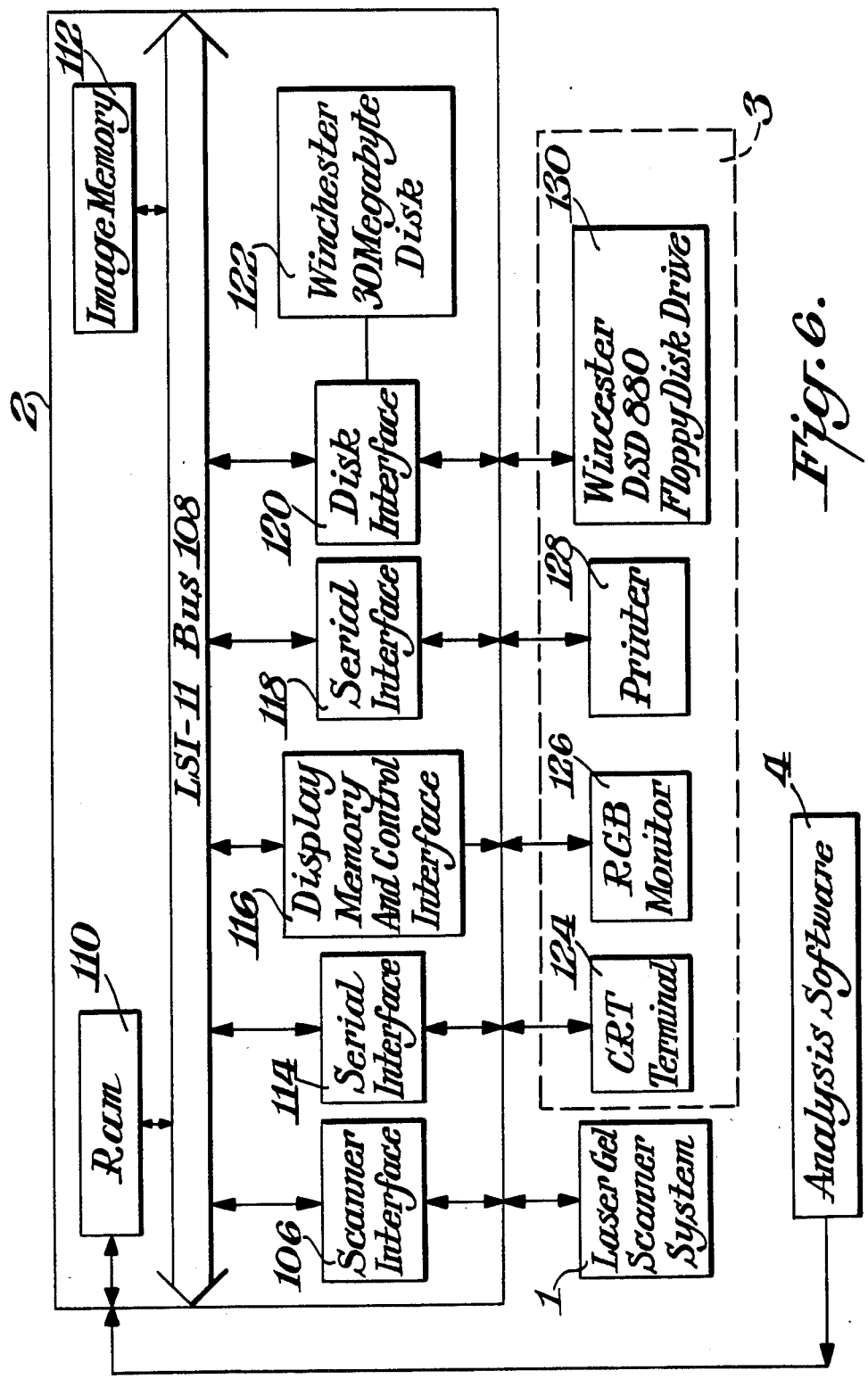
FIG. 6 is a block diagram of the computer depicted in FIG. 1.

The method begins by loading individual array of elements or a pixels defining the image from the scanner, disk, or other storage medium into the image random access memory 110 (FIG. 6). The image is then preprocessed using known techniques, such as described by Lutin et al., so as to render the background substantially zero, and the volumes to be measured as positive quantities. The value of a positive cutoff level is entered. This value represents two surfaces close to a background reference level of the image, one surface on each side of the background. The two surfaces need not be separated from the background by equal distances. The cutoff value is assumed, however, to parametrically control these distances. When all of the image, outside the region between these surfaces has been modeled, the initial modeling step is completed. It is to be understood that, in its most general form, the method of this invention can deal with both positive and negative images, and with varying backgrounds.

Next the pixel having the maximum absolute value of intensity is sought by testing all the image pixels (or with the aid of a look-up table to be described). In the following description the optical density samples of the image i.e., pixels will be represented by integer values of $z(x,y)$ where x and y are cartesian coordinates in the image plane represented as integers.

The absolute value is used in order to detect negative residual peaks that may arise in subsequent steps, as well as the positive peaks present at the beginning. Although the absolute value function is considered here, the concept may be generalized as noted in the foregoing to include two surfaces, one on each side of the background, separated from the background by given distances.

Hence if the maximum absolute value is greater than the preselected cutoff value, the image is searched, starting at the peak pixel position, in the four principal orthogonal cartesian coordinate directions to ascertain the extent of the spot. This extent may differ in all four directions. Once the extent has been determined, an appropriate model is generated and subtracted from the data. Because of the differing extent measurements, the most accurate model needs to be assymetric. This model is assigned a negative amplitude if the maximum found resulted from a pixel having a negative value. In this way, the model is able to describe negative residuals that may have arisen because of earlier overcompensation. This overcompensation arises when the model value exceeds $z(x,y)$ at certain pixels. Overcompensation may also occur when a negative residual is removed by compensation with a negative amplitude model. In this case, the result is a positive residual that is subsequently modeled with a positive-amplitude model.

By an analogy drawn from mechanics, unique model-width parameters are established that incorporate information from all pixels processed. Note that spatial position information concerning every element of mass in a solid body is used in determining the bodies center of mass and amount of inertia properties. By considering the spots as if they were solid bodies, it is apparent that these properties are candidates for spot position and shape measures. The parallel axis theorem provides an elegant method of combining the moments of inertia of separate components of a composite model. More conventional width measures are then more easily obtained from the composite moments. The parallel-axis theorem is used to establish these parameters. The incorporation of all information stands in contrast to the original use of inflection points, which only included information along a swath parallel to each cartesian coordinate axis and passing through the maximum pixel. The virtue of the new parameters for volume, position, and width or extent is that they can be combined in a sensible way in subsequent steps to yield parameters of composite, multi-model spot structures such as would be obtained by direct calculation from the original image data.

After the parameters are determined, they are added to a list. The next maximum of the image, which has been adjusted as just described, is then sought in a repetition of previous steps as indicated in FIG. 2. With each successive subtraction, the absolute-value maximum found decreases, until it is less than the cutoff value and the method terminates. At this point, the total volume under the models represented on the parameter list substantially equals the original volume under the surface $z(x,y)$ and we say that $z(x,y)$ has been adequately parameterized.

In subsequent steps the model volume center coordinates and widths are combined to form single spot composite structures that are characterized by like parameters. It is a property of the analogy with mechanics, i.e., the use of center of mass, and moments of inertia, that allows the combination of all these parameters in a way that results in values that are the same as one would obtain if one computed the parameters directly by their definition from the spot image data alone. The latter technique, however, only works for isolated spots. This method and system has the significant advantage of being able to resolve overlapping spots.

High-resolution 2-D gel-separation technology is believed to offer a key element needed to understand the structure and function of the molecular building blocks underlying life itself. This understanding will lead to improvement in the quality of life through the treatment of disease and alleviation of suffering. The technology of 2-D gel-separation cannot reach its potential without practical methods of spot quantitation.

At present, there are basically two classes of spot quantitation methods:
Modeling methods—spot resolving but inefficient.
Segmentation methods and related types—potentially efficient but non-resolving.

Efficiency and resolving capability are of paramount importance. Spot resolving capability is needed because a significant number of spots on a typical gel overlap. A method that cannot resolve them is limited in applicability. Efficiency is needed because inefficient programs require either long execution time, large expensive computers, expensive array processing hardware, or all of the above. Any of these requirements would make a method impractical for widespread use. The invention disclosed here combines the best feature of both classes of methods, namely *efficiency* and *resolving* capability. It is therefore, believed to hold the key to widespread adoption of not only computerized gel quantitation, but 2-D gel separation technology itself.

METHOD DETAILS

While the method and apparatus of the invention can be used in the quantitation of the spot-like representations of many types such as thin layer chromatograms, radio maps of the sky, or astronomical plates, it is herein described as being used for the quantitation of spots on 2-D electrophoresis gels. The gel optical densities are digitized by the scanner (as will be described) to a desired precision (typically 1 part in 256, ie., 8-Bit encoding is adequate) over an image format of selected density. Typically a 1024×1024 pixel array is satisfactory, although higher densities such as 2048×2048 pixel array may be used merely by the addition of memory.

In the following discussion the reader will wish to refer to the Flow Chart of FIG. 2.

Also, the digital data are corrected to render the spots as positive-going peaks superimposed on a zero-level background. Finally the scanned, corrected spots are stored as an array in a random access memory in a manner that is well known in the art. A cutoff value is then either read from disk or entered by an operator. The cutoff value is chosen to represent two surfaces close to the background reference level of the image, which level is chosen as zero in the present implementation. While the two surfaces need not be equidistant from the background level, they are chosen here to be planes, equidistant from background. When all volume outside the region between these two surfaces is accounted for by models represented on the parameter list, the gel is considered to be adequately quantitated. As stated previously, the mathematical model used may be any model that represents a localized, bounded volume. An assymetric 4-component gaussian is preferred, although certain other assymetric models should probably work nearly as well.

To speed later computation of the model, exponential and square-function look-up tables are generated and stored at this point in the program for future reference. In order to begin the modeling process, the pixel having the largest absolute value in the entire array is first located. If the maximum absolute value is greater than or equal to the cutoff value previously selected, which it certainly should be on this time through the loop, the program goes on to determine the extent of the model. After the algorithm has run for a while, a similarly located maximum absolute value pixel will fall below cutoff and the analysis will terminate.

When using an assymetric gaussian as the model, the inflection points of the data are especially convenient as descriptors of extent of each spot. This arises from the face that, for a Gaussian function, the inflection point occurs precisely one standard deviation from the peak. Thus we obtain four inflection points and generate the mathematical model as will be described. The model is then subtracted from the image. The parameters of the model are placed on a list that may reside on a disk. The next absolute-value maximum is then sought. As noted previously, the algorithm terminates when the maximum absolute-value found is below cutoff.

Next, the various individual models represented by the parameters stored on the parameter list may be combined in appropriate groups representing single spot structures. The method by which these models are combined is generally that described in the prior art by Jansson et al. with several improvements. It is a unique property of the Gaussian parameters V, $\sigma_x$, $\sigma_y$, $\bar{x}$, and $\bar{y}$ that they may be easily combined in a sensible way to form overall spot volumes, width parameters and center-of-mass coordinates. The virtue of this technique, however, lies in its efficiency and applicability to overlapping spots. Its utility stems from the frequent occurrence of such overlapping spots, and the lack of any other efficient method to sensibly allocate volumes between the spots, accurately determine their positions, and accurately determine their width parameters.

In the original Lutin et al. method, and in the simplest version of the present method, the most computer time consuming step is searching the entire image for the maximum absolute-value pixel. To alleviate this problem, a max table that records the maximum absolute-value pixel in each of many separate regions of the image, and its position in each region may be used.

Each time a new absolute-value maximum is needed, it is found merely by searching the max table for the region containing the largest absolute value.

In order that the max table accurately represent the values in the image, it must be updated every time the image values are altered, that is, every time a mathematical model such as a gaussian is subtracted new values must be placed in the max table for all rows affected.

DETERMINING THE INFLECTION POINTS

When the image maximum has been located, the closest inflection points to this maximum in each of the four principal orthogonal coordinate directions are sought; that is, the first inflection points in the $+x$, $-x$, $+y$, and $-y$ directions. Thus far the determination of inflection points is usually done by finding the pixel location where the second partial derivative vanishes. This approach is similar to that taken in the prior art. A finite difference technique is appropriate. Because of the well known propensity for differentiation to emphasize the effects of high-frequency noise in the data, the technique is prone to inaccuracies resulting in the establishment of erroneous locations for the inflection points.

To partially overcome this problem, each pixel along one of the four principal coordinate directions is replaced (for the purpose of inflection-point finding only) by the average of itself and its 6 closest neighbors along a line perpendicular to the principal direction in which the inflection point is sought. This too is described in the prior art. Even this averaging is not sufficient, however, so the prior art stresses the need to filter the entire image before analysis by convolving it with a smoothing function. Unfortunately, these techniques taught by Lutin et al., are a time-consuming procedure.

Overall filtering is avoided by using a method that makes use of the information in neighboring points along the principal direction in which the inflection point is sought. This stands in contrast to the prior art, in which only neighbors perpendicular to the principal directions are employed. Thus, when the inflection point is sought along the principal direction whose pixels have been replaced by averages as noted above, the inflection points are obtained by calculating the second derivative through use of a well known method of simplified least squares. The least-squares method is described by Savitzky, A. And Golay, M. J. E., *Analytical Chemistry*, Vol. 36, No. 8, pg. 1627-1629, July, 1964. The method of this invention therefore makes use of the information in neighboring pixels along the principal direction as well as the information perpendicular to the principal direction, as was described in the prior art.

TWO-DIMENSIONAL ASSYMETRIC GAUSSIAN MODEL

While any model having a shape that localizes a volume may be used in the present algorithm, it is convenient to employ a Gaussian function of the two independent gel-plane coordinates. However, inflection points need not be, and usually are not, at equal distances from the maximum pixel; that is, the $+x$ and $-x$ distances are not equal and the $+y$ and $-y$ distances are not equal. These differences are a natural consequence of the assymetric shape that protein spots typically have. This information is retained by this invention.

Accordingly, this invention employs an assymetric volume model having four characteristic spatial dimensions. In the preferred embodiment, each cartesian quandrant of the Gaussian function is identical to a quadrant of the function described by Lutin, et al. If $\sigma_{x+}$, $\sigma_{x-}$, $\sigma_{y+}$, and $\sigma_{y-}$ are the four principal inflection-point distances from the maximum pixel as noted elsewhere, then the model in this invention is, for the first quadrant, in which both $x-x_o$ and $y-y_0$ are positive, $$z_M(x,y) = A \exp\{-[(x-x_o)/\sigma_{x+}\sqrt{2}]^2\}\exp\{-[(y-y_o)/\sigma_{y+}\sqrt{2}]^2\},$$

for the second quadrant, in which $x-x_o$ is negative and $y-y_o$ is positive, $$z_M(x,y) = A \exp\{-[(x-x_o)/\sigma_{x-}\sqrt{2}]^2\}\exp\{-[(y-y_o)/\sigma_{y+}\sqrt{2}]^2\}.$$

for the third quadrant, in which $x-x_o$ and $y-y_o$ are negative, $$z_M(x,y) = A \exp\{-[(x-x_o)/\sigma_{x-}\sqrt{2}]^2\}\exp\{-[(y-y_o)/\sigma_{y-}\sqrt{2}]^2\},$$

and for the fourth quadrant, in which $x-x_o$ is positive and $y-y_o$ is negative, $$z_M(x,y) = A \exp\{-[(x-x_o)/\sigma_{x+}\sqrt{2}]^2\}\exp\{-[(y-y_o)/\sigma_{y-}\sqrt{2}]^2\}.$$

In the above formulas, $z_M(x,y)$ is the value of the model at the pixel located at the gel plane cartesian coordinates $x$ and $y$, $x_o$ and $y_o$ are the coordinates of the center of the model (which is chosen as the coordinates of the maximum pixel) and A is the amplitude of the model, which is chosen as the value of the maximum pixel that was located as a result of the absolute value search of the image. If the maximum absolute value was located on the negative side of the surface, A is taken to be negative.

The volume of the model is easily obtained by summing the volumes of the four components which, in turn, are easily obtained by either direct integration or from a table of integrals. Thus we find $$V = \frac{\pi A}{2} (\sigma_{x+} + \sigma_{x-})(\sigma_{y+} + \sigma_{y-}).$$

Because the Gaussian model falls to a relatively small value within a relatively short distance from its center coordinates of $(x_o, y_o)$, the model is evaluated and subtracted from the image only within a rectangle in which this operation would cause significant alteration of the image. Therefore, computation time is greatly reduced as compared with that which would be required to evaluate the model over the entire image plane. The boundaries of the rectangle may be usefully specified as the vertical straight lines located at $$x = x_o + \sigma_{x+} \sqrt{\ln A} \text{ and } x = x_o - \sigma_{x-} \sqrt{\ln A},$$

and the horizontal straight lines located at $$y = y_o - \sigma_{y-} \sqrt{\ln A} \text{ and } y = y_o + \sigma_{y+} \sqrt{\ln A}.$$

In order to save time, the model may be computed with the aid of look-up tables, thereby eliminating repeated computation of the exponential expression for each pixel in each model. In the method of this invention, the tables are established before beginning the analysis. The two principal computations that are time-consuming in generating the model are the exponential function and the square operation, so two tables are employed.

SUBTRACTING THE MODEL AND CALCULATING ITS PARAMETERS

When the model is subtracted from the image surface, negative regions result that represent overcompensation for the image values. This effect occurs at all pixel locations at which the values of the model $z_M(x,y)$ exceed the value of the pixel $z(x,y)$. As subtraction is carried out at each pixel, the image is updated by replacing each image value $z(x,y)$ by $z(x,y) - z_M(x,y)$. These negative regions are eliminated by subsequent models having negative amplitude. Two questions are next presented: (1) What should be considered to be the center of each model? and (2) How does one characterize it's width in a simple way such that when multiple models are later combined into single spot entities, the width parameters retain a sensible meaning?

These questions are answered as described in the copending Elias et al. application by an analogy to the dynamics of rotating bodies, particularly the physical properties that are used in characterizing their motion.

To determine the center of a spot, this model may be considered as if it had mass, of a uniform density within the volume defined by a local peak of $z(x,y)$. One may obtain the model center of mass by computing $$\bar{x} = x_o + \sqrt{2/\pi} (\sigma_{x+} - \sigma_{x-}),$$

and $$\bar{y} = y_o + \sqrt{2/\pi} (\sigma_{y+} - \sigma_{y-}).$$

It is known that the moments of inertia of physical bodies can be combined provided that the moments about their respective centers of mass are known, and that the coordinates of the spatial distribution of masses is known. This may be done with the parallel-axis theorem of mechanics. The result of such a combination is a moment of inertia of the aggregate masses about their common center of mass.

The applicability of the analogy becomes clearer when one realizes that the moment of inertia is given by the simple product of the volume and variance $\sigma^2$. (Note that in the case of a perfect gaussian, the variance is the inflection-point distance squared). By knowing the centers of mass of each of the four components of the model and applying the parallel-axis theorem, the aggregate moment of inertia may be determined about the four-component aggregate center of mass. Once that moment is obtained, the variance results by dividing the moment by the aggregate mass. By following this procedure it is easy to derive the variances of a four-component Gaussian model about it's center of mass:

$$\sigma_x^2 = [(1 - 2/\pi)(\sigma_{x+}^2 + \sigma_{x-}^2) + (4/\pi - 1)\sigma_{x+}\sigma_{x-}]$$

$$\sigma_y^2 = [(1 - 2/\pi)(\sigma_{y+}^2 + \sigma_{y-}^2) + (4/\pi - 1)\sigma_{y+}\sigma_{y-}].$$

PEAK COMBINING

After the modeling algorithm has completed its work and substantially all the integrated optical density (volume) under the surface $z(x,y)$ has been accounted for in the positive and negative values of V stored on the parameters list, the various single models represented by the parameters stored on the parameter list may be combined in appropriate groups representing single spot structures. It is the unique property of the parameters V, $\sigma_x$, $\sigma_y$, $\bar{x}$ and $\bar{y}$ that they too may be easily combined in a sensible way to form overall spot volumes, width parameters, and center of mass coordinates. The prior art (Jansson et al.) describes the preferred human-interactive peak-combining method of selecting gaussians to be included in the composite model for each spot.

This method employs a digital-refreshed-raster display to represent the models as colored crosses superimposed on the spot pattern image. As the operator selects models to be incorporated into each spot composite, the colors of the crosses are altered to show which model has been selected.

The method presently employed is identical to the prior art except for the following refinement:
(1) The plus-arm lengths determined by the four standard deviations $\sigma_{x+}$, $\sigma_{x-}$, $\sigma_{y+}$, and $\sigma_{y-}$ are now displayed instead of the 1/e points described in the prior art.
(2) The console terminal numeric keypad has replaced the joystick as a means of positioning the cursor,
(3) A different display system is being used that, in this instrument, performs the same function as in the system described in the prior art,
(4) The standard deviations $\sigma_x$ and $\sigma_y$ of the spot are computed with the aid of the parallel-axis theorem by referring to the moment-of-inertia analogy employed earlier.

Explicitly, assume that one is given the parameters for N gaussians where the parameters for the $i^{th}$ gaussian are expressed as $(V)_i$, $(x_{CM})_i$, $(y_{CM})_i$, $(\sigma_x)_i$, $(\sigma_y)_i$.

Note: (Parentheses and the subscript i have been added to the notation previously introduced to signify that the parameters correspond to the $i^{th}$ gaussian.)

The parameters for the spot comprising the N gaussians may then be obtained as follows. The volume of the spot is given by $$\overline{V} = \sum_i (V)_i.$$

The center of mass of the spot is given by $$\overline{x}_{CM} = \sum_i (x_{CM})_i (V)_i / \overline{V}$$

and $$\overline{y}_{CM} = \sum_i (y_{CM})_i (V)_i / \overline{V},$$

respectively. The x and y standard deviations of the spot are given by $$\overline{\sigma}_x = \left\{ \left[ \sum_i (V)_i \{(\sigma_x)_i^2 + [\overline{x}_{CM} - (x_{CM})_i]^2\} \right] / \sum_i (V)_i \right\}^{\frac{1}{2}}$$

and $$\overline{\sigma}_y = \left\{ \left[ \sum_i (V)_i \{(\sigma_y)_i^2 + [\overline{y}_{CM} - (y_{CM})_i]^2\} \right] / \sum_i (V)_i \right\}^{\frac{1}{2}}$$

respectively. The results obtained by these formulas are the same as those that would have been obtained by computing the volumes, center-of-mass coordinates, and standard deviations directly from the spot data, for one isolated spot, by use of their respective definitions.

By using the above methods of quantitation and peak combining, however, two substantial advantages are gained:

(1) One is able to correctly characterize spots that are partially overlapping and, (2) Computer-time-consuming explicit summations involving individual pixel values are entirely avoided. The models account completely for contributions elsewhere. The advantage of applicability to overlapping spots has special significance because of the frequent occurrence of such spots.

The above-described spot parameters result from contributions over the *entire* spot. They are measures of volume, location, and shape, respectively, that draw upon *every optical density measurement in the spot*, and are, therefore, *truly* representative. Because they are integral measures, they exhibit the precision and noise-minimizing properties that are characteristic of averaging processes.

Furthermore, these means are seen to successfully solve the problems of accuracy, precision, efficiency, and resolving capability. In appendix I there is displayed a Fortran program to quantitate an image according to the method described in the foregoing. For clarity, the use of look-up tables for both absolute-value maximum location, and for model generation have been omitted in this example.

II. LASER GEL SCANNER

The laser gel scanner that has been used successfully to provide the image data processed by this invention will be described in three parts: The beam focusing and directing optics (FIG. 3), the gel scanner mechanical assembly (FIG. 4); and the gel scanner electronics and data interface system (FIG. 5). It is to be understood, however, that any suitable image or radiation scanning system can be used. The subject invention is concerned only with the processing of spot image data to quantitate the spots.

BEAM FOCUSING AND DIRECTING OPTICS

Refering to FIGS. 3 and 4, the laser scanner uses a low powered He-Ne laser 5 as the source of a focused laser beam 29 that is swept rapidly in a transverse direction relative to the line of movement of a gel such that the focal line is adjacent to, but not coincidental with, the gel surface. This is done in order to obtain an optimal beam spot size. In describing the optical train the laser 5, typically a 5 mW He-Ne source, produces a substantially parallel beam 29 which is focused by lens 7 to a point between respective first and second folding mirrors 10, 12. A beam splitter 6 is interposed between lens 7 and first folding mirror 10 to direct a portion of the beam to a reference photodiode 8, which in turn, generates a reference signal input for the optical density analyzer. The laser beam, after being reflected from the second folding mirror 12, passes to a second lens 14, which in turn, brings the beam to a focus at a point near, but not necessarily on, the gel plane 24.

A scan mirror 16, driven by galvo (galvanometer) scanner 18, scans the focused beam across a third and fourth folding mirrors 20, 22 in series and thence to the long-line photodiode sensor 28, typically a $9'' \times \frac{1}{4}''$ Shottky photodiode manufactured by United Detector Technology. The third and fourth folding mirrors 20, 22 have been positioned after the scan mirror 16 to lengthen the scan radius sufficiently to maintain (within 2.5 degrees) the perpendicularity of the scan beam to the gel plane 24 throughout the extent of each scan. This is done so as to avoid the effects of apparent changes in optical density in the plane 24 as the scan is generated. As a further measure to enhance the uniformity of response of this detector 28 a strip of opal glass 26 is positioned adjacent to the photosensitive surface to diffuse the light, thereby averaging and minimizing the effect of any nonuniformities that may be present.

If the beam is truly perpendicular to the gel at any beam position, say at the center of the scan, then optical interference may corrupt the data due to the appearance of fringes superimposed on the image. The interference arises because the direct beam and the beam internally reflected in the plate and/or gel are coaxial when the beam is perpendicular. This interference problem is avoided by adjusting the geometry of the beam deflection so that the beam is not perpendicular at any beam position during the scan. This condition is obtained by inclining the beam slightly in the plane that is perpendicular to both the gel plane and the plane that is defined by the beam sweep.

GEL SCANNER MECHANICAL ASSEMBLY

The optics depicted in FIG. 3 are shown in place in the pictorial illustration of FIG. 4. The laser gel scanner has been designed specifically to digitize the two-dimensional optical density information in 2-D gels. However, it will digitize any substantially transparent object, possibly containing absorbing or light scattering regions, provided that the object dimensionally fits on a gel stage 30. Wet and dry gels as well as autoradiograms may be scanned. The maximum gel size is 200×240 mm.

Refering to FIG. 4, the gel stage 30 is a rectangular-shaped frame that is designed to accomodate a glass gel holder, typically 200×240×9 mm., and transport it in the gel plane through the scan zone. When the unit scans wet gels, a glass gel holder with a raised lip (not shown) around the edge is typically used to confine the liquid. A glass cover plate (not shown) is also often used to flatten the gel surface. The gel stage 30 is designed to be introduced into the scanner assembly 39 which includes a base plate 41 and a pair of end plates 43 supported by rods 45. The various components of the optical system are located at various points on this assembly to form the folded beam, compact scanning system.

The scan zone is defined as that region in the gel plane that lies between the long-line photo sensor 28 and fourth folding mirror 22. The gel stage 30 comprises two apertured aluminum support plates 34, 36 that are connected by aluminum support tubes 38, 40. The stage 30 is mounted to slide along two steel support rods 42, 44 which define the gel plane so that the stage can be drawn through the scan zone by a continuous pulley 47, mounted pull string 46, the ends of which are secured to the stage at opposing attachment points 48. Pull string 46 is typically a high tensile-strength stainless-steel cable to minimize effects of both thermal and mechanical stresses on its elongation. Stage-position detectors 50 comprise pairs of LEDs and photosensors to signal when the stage is in either the "begin-scan", or "end of scan" positions.

Stage motor 32, typically a 1 RPM instrument gear motor with a constant speed and reversible field, is attached to the exterior surface of one of the two end plates 43 for the scanner assembly and turns drive capstan 52 which is keyed to the motor shaft. Pull string 46 is tightly wrapped around capstan 52, at least four times, for positive traction so that as the capstan turns, the stage translates smoothly through the scan zone in the signalled direction, at a constant speed. Simultaneously, it is transversely scanned by the scanning beam which passes through the gel to the diode sensor 28.

GEL SCANNER ELECTRONICS AND DATA INTERFACE SYSTEM

Figure 5A:
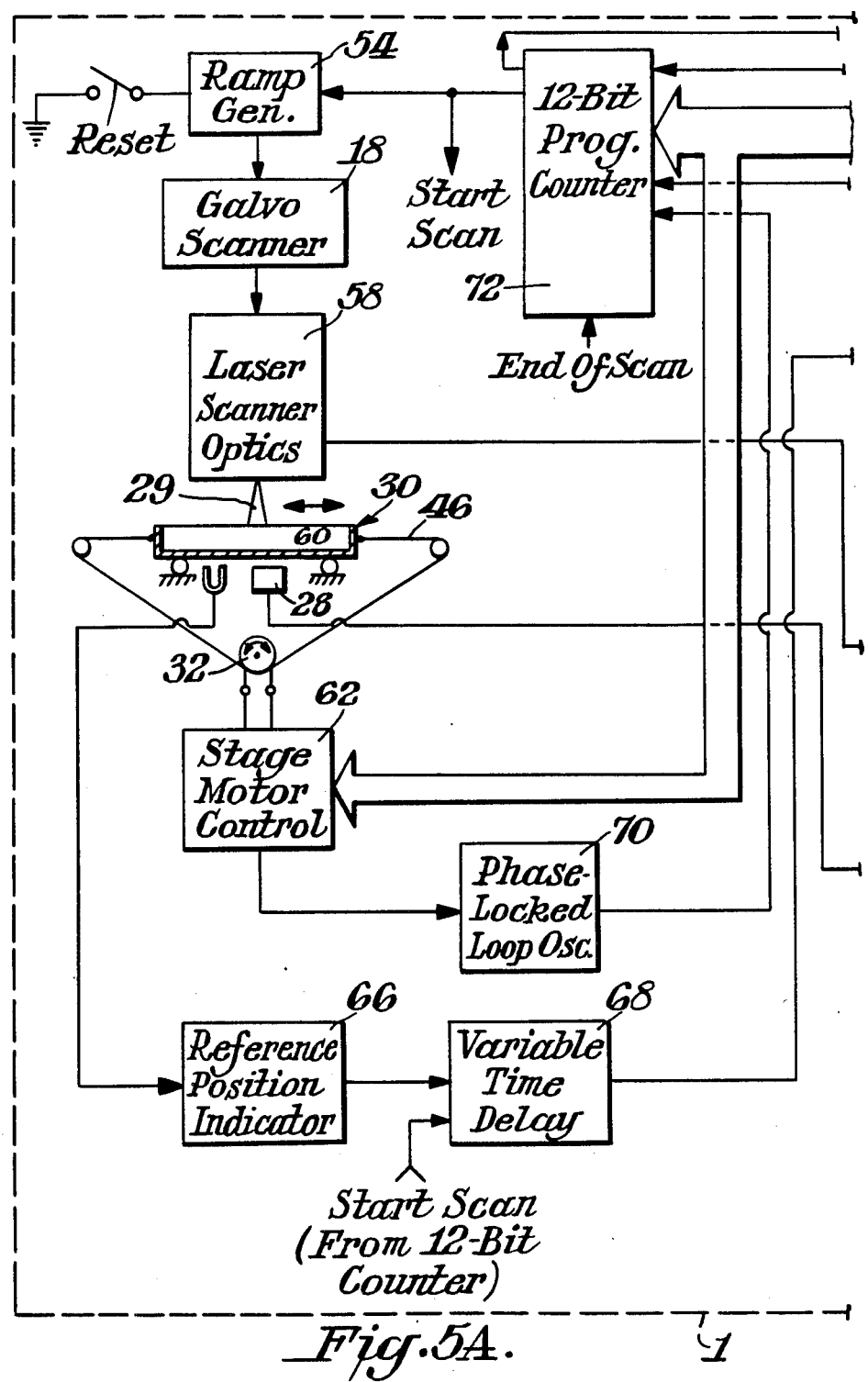
FIGS. 5A and 5B are block diagrams of the scanner electronics and data interface system used in this invention.
Figure 5B:
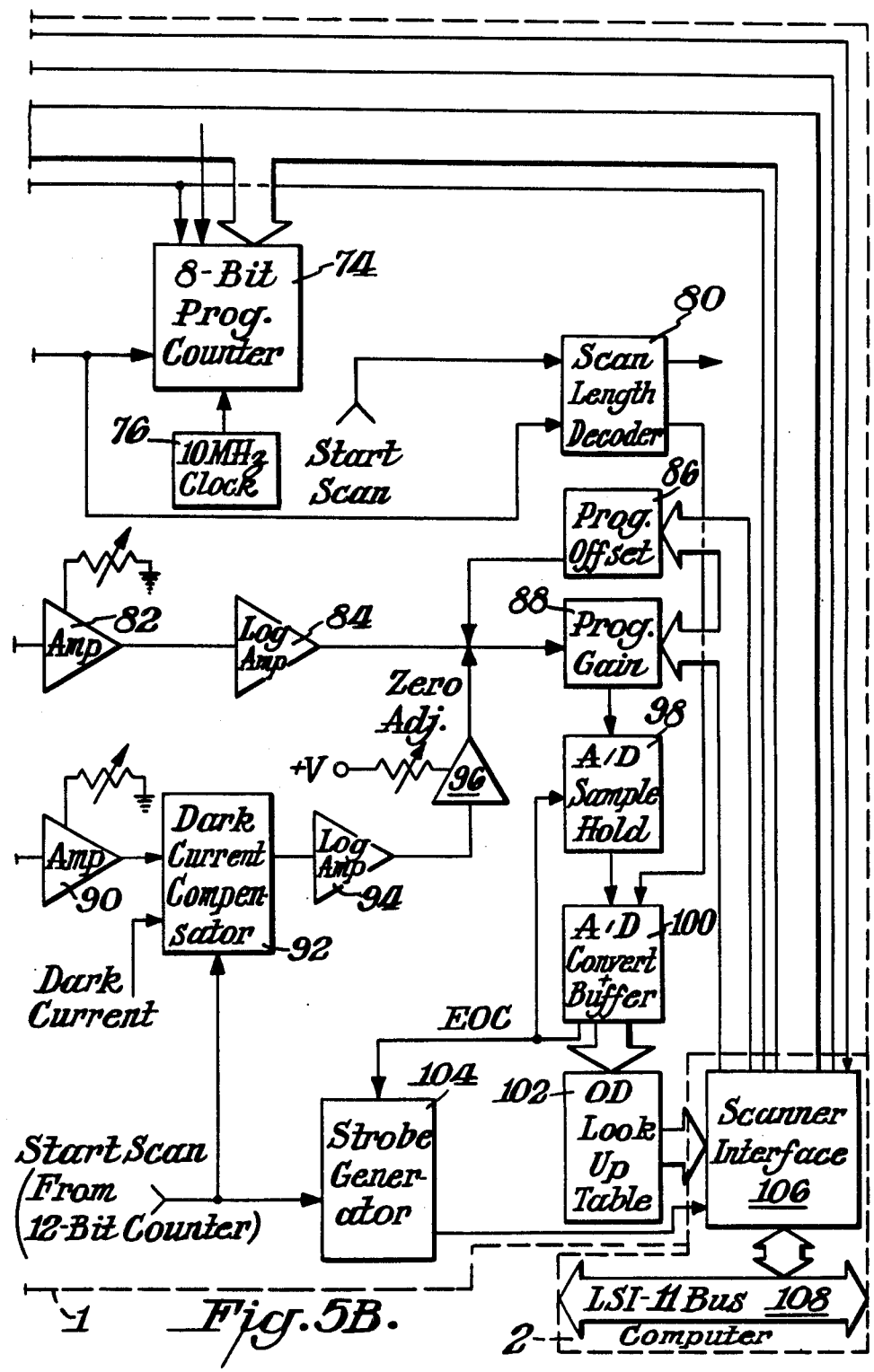

Depicted in FIGS. 5A and 5B are block diagrams of the gel scanner and data interface system. The laser gel scanner system 1 interfaces the computer 2 via a scanner interface 106 which in turn interfaces an LSI-11 Bus 108. All communication to the scanner system is conducted through the scanner interface 106. Thus, the computer controls the stage motor control 62, a 12-Bit programmable counter 72, an 8-Bit programmable counter 74, a programmable gain circuit 88, and a programmable offset circuit 86. These functions are all interrelated such that the laser scanner precisely scans the gel in a fashion that enables the two-dimensional optical density information to be digitized for use during analysis by the software.

In order to provide precise synchronization between the stage position and the initiation of each scan, zero-crossings of the stage motor 32 supply voltage waveform are used to toggle a 6 kHz phase-locked loop oscillator 70 which, in turn, clocks a row-spacing 12-Bit programmable counter 72. The synchronized periodic start-scan signals produced by the 12-Bit counter 72 are spaced according to instructions programmed by the operator via the scanner interface 106 to establish row spacing, and the separation between successive scan lines.

More specifically, the start scan signal does the following:

1. It causes the galvanometer ramp generator 54, to produce a saw-tooth waveform needed to deflect the galvanometer scanner mirror 16 (FIGS. 3 and 4) and sweep the laser beam across a gel 60 in the gel stage 30. The ramp generator 54 is provided with a manual reset switch that may be used to stop the scan without affecting the stage movement.

2. It enables the variable time delay circuit 68 such that it is ready to respond to the reference-position indication signal from the reference-position indicator 66, which is coupled to the reference-position photodetector 8. The variable time-delay circuit 68 provides the means by which the operator can manually select a prescribed portion of the gel (in terms of pixels in the scan direction, or columns) to be scanned.

3. When combined with the output of the column-spacing 8-Bit programmable counter 74 it provides the enabling signal for the scan-length decoder 80. The 8-Bit column counter 74 performs a similar function as the 12-Bit programmable counter 72 in that it receives pixel-spacing information from the operator via the scanner interface 106 and signals the occurrence of the end of each scan to the scan length decoder 80. The scan-length decoder 80 generates (a) an end of scan signal and transmits it to the 12-Bit programmable counter 72, which in turn, transmits a clear address signal to the scanner interface 106, and (b) a convert signal to the A/D converter 100. A 10 MHz clock 76 is used to increment the 8-Bit column-spacing counter 74. The scanner interface 106 transmits scan enable and counter load signals to the respective counters.

4. The start-scan signal also activates the dark current compensator 92 for measuring a representative photodetector dark current/voltage from the gel-free portion of the scan for subtraction from the instantaneous analytical signal for calibration purposes.

5. Finally, the start-scan signal enables each EOC (End of Convert) status signal to strobe 104 the A/D converted data via the A/D converter 100 in the buffer registers 100 into the scanner interface 106.

The last circuit to be described is the OD (Optical Density) analyzer. The principal inputs to this circuit are the reference signal and the analytical signal which are obtained from the action of the galvo deflector 18 passing the scanning laser beam through the laser scanner optics 58 through the gel 60 onto the long-line photodetector 28. In addition, programmable gain 88 and programmable offset 86 parameters are input to this circuit from the computer via the scanner interface 106. These parameters are used to optimize the digitization of pixel OD values.

In operation the reference and analytical signals are separately amplified logarithmically via the operational amplifier 82, 84 in the reference line and 90, 94 in the analytical line. These signals are then summed with the programmed offset value at a summing junction where the log (A/R) result is formed. Manual controls are provided for the operator to make zero-adjust corrections 96 to the analytical signal prior to its appearance at the summing junction. The settings are made based on OD values existing at the outset of each scan in the calibration series.

The programmable-gain circuit 88 is configured to enable the operator to manually select either high or low OD ranges and make full-scale adjustments for them upon prompting by the computer should the operator know ahead of time what high and low OD limits are needed for the gel to be scanned. This feature is provided in addition to its normal function of automatically applying gain values to the ratio signals present at the summing junction using values transmitted to it from the scanner interface 106.

The A/D sample/hold circuit 98 samples the scan signals at a programmed rate, and transmits the held voltages directly to the A/D converter 100 for processing into 8-Bit format. The output data terminals of the A/D converter are connected to a set of buffer registers for storing each scan's data in 12-Bit format. The buffer register output terminals are in turn connected to a lookup table memory 102, which communicates the digitized OD values to the scanner interface 106, the OD values are represented by eight data bits.

The A/D converter 100 responds to a convert signal that is generated by the scan-length decoder 80 at the end of each scan. Upon its receipt, the A/D converter 100 loads the buffer registers and generates end of convert (EOC) signal pulses to the A/D sample/hold 98 and strobe-generator circuits 104 to simultaneously load new data into the A/D converter 100 while the preceeding scan's data is entered onto the computer via the scanner interface 106.

During the operation of the scanner, a reference position indicator 66 is positioned at one of the scan extremes to sense the beginning of each scan needed to initiate the operation of the scanner/stage motor controller 62. A split photodector 50 has been found useful for this purpose by generating a sharply rising trigger pulse that contributes substantially to the precision of scan direction displacement (column) measurements.

III. COMPUTER SYSTEM

The last module which will be discussed in detail is the computer system 2 and 3 (FIG. 1) used with the gel scanner. Illustrated in FIG. 6 is a detailed block diagram of the computer 2, the interface modules 106, 114, 116, 118, 120 its peripherals and memory module 110, 112. The system's peripherals includes blocks 124, 126, 128, 130, the analysis software 4 and the computer memory modules 110, 112. The LSI-11 Bus 108 serves as the main communication link to all the major system components.

The computer serves many functions, several of which are specific to 2-D gel analysis. It transmits the scan parameters to the scanner interface 106 which in turn passes these parameters to the gel scanner 1. It both receives and transmits data from the various peripheral interfaces 114, 116, 118, 120 to the associated system peripherals 124, 126, 128, 130 which are directly accessible by the operator. It processes the 2-D gel data using the analysis software 4 that resides in the main Random-Access Memory 110 and interacts with the image memory 112 during system operation. In addition, the computer controls the movement of data to and from the major components of the system via the LSI-11 data Bus 108. Each of these major components will be described in more detail below.

The computer 2, is a DEC (Digital Equipment Corporation) LSI-11/23 microcomputer with 256K bytes of main memory. The operating system is DEC's single-user system, RT-11 version 4. The computer uses the Random-Access Memory 110 to store both programs and data. As mentioned above the LSI-11 Bus 108 serves as the main communication link to all the major system components.

The image-memory system 112 has been designed to store over four million 8-Bit samples per circuit board with integrated-circuit memories now readily available. The amount of data generated by the laser scanner system 1 is relatively large, at present typically over one million samples. These data must be stored in a place where access to them is random and rapid. The image memory 112 provides this function as follows. The image memory 112 which, consists of commercially available components, utilizes a 2048 word-wide address-window of the DEC LSI-11/23 computer 2 located in the I/O portion of the memory physical address space as the location where the scanned image data are accessed. This section of the I/O memory addresses is used to access a single horizontal line of pixels, all of which are contained in the image memory 112. The horizontal line appearing in the 2048 word window is specified by a number in a single register in a neighboring area of the I/O address region. Different lines may be made to appear in the 2048 word window by changing the horizontal line pointer in this register.

The system peripherals 3 are detailed in FIG. 6 as items 124, 126, 128 and 130. An interface module 114, 116, 118, and 120 is associated with each peripheral as a means for providing the correct communications link between the computer Bus 108 and the operator. The CRT terminal 124 is a conventional terminal used by the operator to control the operation of the laser gel scanner instrument. The interface associated with the terminal is an RS-232 serial interface 114 which is linked directly to the LSI-11 Bus 108. The RGB monitor 126 is a color display monitor that accepts an RS-170 video signal from the display memory and control interface 116 via the LSI-11 Bus 108. The display memory and control interface 116 stores a portion of the gel image which is continuously displayed on the RGB monitor 126. The display memory array is arranged as 480 rows with 512 picture elements (pixels) per row. Both the RGB monitor 126 and the display memory and control interface are commercially available. The printer 128 and its serial interface 118 both of which are commercially available, are used to generate hard copy information generated as a result of the gel analysis. A Winchester DSD 880 Floppy Disk drive 130, a disk interface 120 and the Winchester 30 megabyte disk 122 in combination provide the system with an adequate amount of data mass-storage capability.

The method and apparatus of this invention are thus seen to provide a rapid, efficient means of resolving and quantitating image spot information from whatever source derived.

APPENDIX 1

```
      SUBROUTINE S2 SIDE(ICUT)
C
C     THIS SUBROUTINE USES THE DUAL-SIDED MAXIMUM SEARCH METHOD
C     TO QUANTITATE A SPOT IMAGE CONTAINED IN THE 100X100 ARRAY
C     IZ.  THE DATA ARE ASSUMED TO REPRESENT POSITIVE-GOING SPOTS
C     ON A SUBSTANTIALLY ZERO BACKGROUND.  THE ARGUMENT ICUT
C     SPECIFIED BY THE CALLING ROUTINE SETS THE CUTOFF LEVEL.
C
C     IZ              INTENSITY SAMPLES OF IMAGE (PIXEL VALUES)
C
C     IA              PEAK AMPLITUDE OF GAUSSIAN MODEL
C
C     ISXP, ISXM      PRINCIPAL INFLECTION POINT DISTANCES
C     ISYP, ISYM      FROM THE MAXIMUM ABSOLUTE VALUE PIXEL
C
C     IX0, IY0        COORDINATES OF THE GAUSSIAN-MODEL CENTER
C
C     ICUT            CUTOFF VALUE OF INTENSITY
C
C     SSQX, SSQY      VARIANCES OF A 4-COMPONENT GAUSSIAN MODEL
C                     ABOUT ITS CENTER OF MASS
C
C
C
      COMMON IZ(100,100),IA,ISXP,ISXM,ISYP,ISYM,IX0,IY0
      PI=3.1416
C
C
C     FIND MAXIMUM ABSOLUTE VALUE PIXEL
 30   CALL MMAX
C
C     IS IT LESS THAN OR EQUAL TO CUTOFF?  IF SO, END ANALYSIS.
      IF(ABS(IA).LE.ICUT) GO TO 90
C
C     OTHERWISE CONTINUE
C
C     FIND EXTENT OF MODEL BY USING INFLECTION POINTS
      CALL EXTENT
C
C     GENERATE AND SUBTRACT A GAUSSIAN MODEL
      CALL SUBTRA(ICUT)
C
C     CALCULATE CENTER OF MASS AND SIGMAS
      XBAR=IX0+SQRT(2./PI)*(ISXP-ISXM)
      YBAR=IY0+SQRT(2./PI)*(ISYP-ISYM)
      SSQX=((1.-2./PI)*(ISXP**2+ISXM**2)+(4./PI-1.)*ISXP*ISXM)
      SSQY=((1.-2./PI)*(ISYP**2+ISYM**2)+(4./PI-1.)*ISYP*ISYM)
C
C     OUTPUT THE PARAMETERS
      WRITE(6,9000)IA,ISXP,ISXM,ISYP,ISYM,IX0,IY0,XBAR,YBAR,
     1 SSQX,SSQY
 9000 FORMAT(1X,7I4,4F10.2)
C
C     FIND NEXT MAX
      GO TO 30
C
 90   CONTINUE
      END
```

```
      SUBROUTINE MMAX
      COMMON IZ(100,100),IA,ISXP,ISXM,ISYP,ISYM,IX0,IY0
C
C     FIND MAXIMUM ABSOLUTE VALUE IN IMAGE
      IA=0
      DO 600 IY=1,100
          DO 500 IX=1,100
              IAABS=IABS(IZ(IX,IY))
              IF(IAABS.GT.IA)GO TO 300
              GO TO 400
300           CONTINUE
              IA=IAABS  !HERE IA HAS ONLY POS. SIGN
              IX0=IX
              IY0=IY
400           CONTINUE
500       CONTINUE
600   CONTINUE
      IA=IZ(IX0,IY0) !GETS PROPERLY SIGNED IA
      RETURN
      END
      SUBROUTINE EXTENT
C
      COMMON IZ(100,100),IA,ISXP,ISXM,ISYP,ISYM,IX0,IY0
C
C     SEEK INFLECTION POINT IN +X DIRECTION
C
C     IF NEAR EDGE OF IMAGE, ASSIGN DEFAULT INFLECTION POINT
      IF(IX0.GT.100-3) GO TO 110
      GO TO 120
110       CONTINUE
          ISXP=MAX(100-IX0,1)
          GO TO 190
C
C     ELSE SEEK IT PROPERLY
120       CONTINUE
          IX=IX0 !FIRST PLACE TO EVALUATE 2ND DERIVATIVE
C         IF TOO CLOSE TO OTHER EDGE, STEP OUT AS FAR AS NEEDED
          IF (IX0.LT.2)IX=2
C         SIGN OF 2ND DERIVATIVE AT CENTER IS SAME AS SIGN
C            OF IMAGE AT MAX
          ISMAX=ISIGN(1,IZ(IX0,IY0))
C
C         DO UNTIL SIGN CHANGES OR EDGE IS REACHED
150           CONTINUE
              IX=IX+1
              IS=-ISIGN(1,
     1             2*IAVG7(2,IX-2,IY0)
     1            -1*IAVG7(2,IX-1,IY0)
     1            -2*IAVG7(2,IX  ,IY0)
     1            -1*IAVG7(2,IX+1,IY0)
     1            +2*IAVG7(2,IX+2,IY0))
              IF(IS.EQ.ISMAX.AND.IX.LE.100-3) GOTO 150
          ISXP=IX-IX0
190       CONTINUE
C
C     SEEK INFLECTION POINT IN -X DIRECTION
C
C     IF NEAR EDGE OF IMAGE, ASSIGN DEFAULT INFLECTION POINT
      IF(IX0.LT.4) GO TO 210
      GO TO 220
210       CONTINUE
          ISXM=MAX(IX0-1,1)
          GO TO 290
C
```

```
C         ELSE SEEK IT PROPERLY
 220              CONTINUE
                  IX=IX0   !FIRST PLACE TO EVALUATE 2ND DERIVATIVE
C                 IF TOO CLOSE TO OTHER EDGE, STEP OUT AS FAR AS NEEDED
                  IF (IX0.GT.100-1)IX=100-1
C                 SIGN OF 2ND DERIVATIVE AT CENTER IS SAME AS SIGN
C                    OF IMAGE AT MAX
                  ISMAX=ISIGN(1,IZ(IX0,IY0))
C
C                 DO UNTIL SIGN CHANGES OR EDGE IS REACHED
 250              CONTINUE
                  IX=IX-1
                  IS=-ISIGN(1,
      1               2*IAVG7(2,IX-2,IY0)
      1              -1*IAVG7(2,IX-1,IY0)
      1              -2*IAVG7(2,IX  ,IY0)
      1              -1*IAVG7(2,IX+1,IY0)
      1              +2*IAVG7(2,IX+2,IY0))
                  IF(IS.EQ.ISMAX.AND.IX.GE.4) GOTO 250
                  ISXM=IX0-IX
 290              CONTINUE
C

C
C         SEEK INFLECTION POINT IN +Y DIRECTION
C
C         IF NEAR EDGE OF IMAGE, ASSIGN DEFAULT INFLECTION POINT
          IF(IY0.GT.100-3) GO TO 310
                  GO TO 320
 310              CONTINUE
                  ISYP=MAX(100-IY0,1)
                  GO TO 390
C
C         ELSE SEEK IT PROPERLY
 320              CONTINUE
                  IY=IY0   !FIRST PLACE TO EVALUATE 2ND DERIVATIVE
C                 IF TOO CLOSE TO OTHER EDGE, STEP OUT AS FAR AS NEEDED
                  IF (IY0.LT.2)IY=2
C                 SIGN OF 2ND DERIVATIVE AT CENTER IS SAME AS SIGN
C                    OF IMAGE AT MAX
                  ISMAX=ISIGN(1,IZ(IX0,IY0))
C
C                 DO UNTIL SIGN CHANGES OR EDGE IS REACHED
 350              CONTINUE
                  IY=IY+1
                  IS=-ISIGN(1,
      1               2*IAVG7(1,IX0,IY-2)
      1              -1*IAVG7(1,IX0,IY-1)
      1              -2*IAVG7(1,IX0,IY  )
      1              -1*IAVG7(1,IX0,IY+1)
      1              +2*IAVG7(1,IX0,IY+2))
                  IF(IS.EQ.ISMAX.AND.IY.LE.100-3) GOTO 350
                  ISYP=IY-IY0
 390      CONTINUE
C
C         SEEK INFLECTION POINT IN -Y DIRECTION
C
C         IF NEAR EDGE OF IMAGE, ASSIGN DEFAULT INFLECTION POINT
          IF(IY0.LT.4) GO TO 410
                  GO TO 420
 410              CONTINUE
                  ISYM=MAX(IY0-1,1)
                  GO TO 490
C
```

```
C        ELSE SEEK IT PROPERLY
420              CONTINUE
                 IY=IY0  !FIRST PLACE TO EVALUATE 2ND DERIVATIVE
C                IF TOO CLOSE TO OTHER EDGE, STEP OUT AS FAR AS NEEDED
                 IF (IY0.GT.100-1)IY=100-1
C                SIGN OF 2ND DERIVATIVE AT CENTER IS SAME AS SIGN
C                   OF IMAGE AT MAX
                 ISMAX=ISIGN(1,IZ(IX0,IY0))
C
C                DO UNTIL SIGN CHANGES OR EDGE IS REACHED
450                 CONTINUE
                    IY=IY-1
                    IS=-ISIGN(1,
     1                  2*IAVG7(1,IX0,IY-2)
     1                 -1*IAVG7(1,IX0,IY-1)
     1                 -2*IAVG7(1,IX0,IY  )
     1                 -1*IAVG7(1,IX0,IY+1)
     1                 +2*IAVG7(1,IX0,IY+2))
                    IF(IS.EQ.ISMAX.AND.IY.GE.4) GOTO 450
                 ISYM=IY0-IY
490              CONTINUE
C
         RETURN
         END
         FUNCTION IAUG7(IXORY,IX,IY)
C
C
C        THIS FUNCTION AVERQAGES A ROW (OR COLUMN) OF 7 NUMBERS
C        CENTERED ABOUT THE PIXEL AT (IX,IY) IN THE X (OR Y) DIREC-
C        TION.  IF IXORY IS 1, A ROW AVERAGE IS OBTAINED.  IF IXORY
C        IS 2, A COLUMN AVERAGE IS OBTAINED.
C
C
         COMMON IZ(100,100),IA,ISXP,ISXM,ISYP,ISYM,IX0,IY0
         IAVG7=0
         IF (IXORY.EQ.1) GO TO 20  !ROW AVERAGE
                 GO TO 60
20               CONTINUE
                 IS=MAX(IX-3,1)
                 IFI=MIN(IX+3,100)
                 DO 40 I=IS,IFI
                        IAVG7=IAVG7+IZ(I,IY)
40               CONTINUE
                 GO TO 80
C
C        ELSE
60               CONTINUE
                 IS=MAX(IY-3,1)
                 IFI=MIN(IY+3,100)
                 DO 70 I=IS,IFI
                        IAVG7=IAVG7+IZ(IX,I)
70               CONTINUE
80               CONTINUE
         ITOT=IFI-IS+1
         IAVG7=IFIX(FLOAT(IAVG7)/FLOAT(ITOT)+0.5)
         RETURN
         END
         SUBROUTINE SUBTRA (ICUT)
         COMMON IZ(100,100),IA,ISXP,ISXM,ISYP,ISYM,IX0,IY0
         SQRT2=SQRT(2.)
         FIA=FLOAT(IABS(IA))
         ISI=ISIGN(1,IA)
C
```

```
C       ESTABLISH LIMITS OF SUBTRACTION
C       DIVISOR OF FIA ESTABLISHES SUBTRACTION OVER REGION WHERE
C       GAUSSIAN HAS VALUE GREATER THAN CUTOFF
        CONST=SQRT(2.*ALOG(FIA/FLOAT(ICUT)))
        IXP=IX0+ISXP*CONST+0.5
        IXM=IX0-ISXM*CONST+0.5
        IYP=IY0+ISYP*CONST+0.5
        IYM=IY0-ISYM*CONST+0.5
C
C
C       BE SURE EDGES OF IMAGE ARE NOT EXCEEDED
        IXP=MIN(IXP,100)
        IXM=MAX(IXM,1)
        IYP=MIN(IYP,100)
        IYM=MAX(IYM,1)
C
C
C       GENERATE AND SUBTRACT 4-COMPONENT GAUSSIAN
        DO 500 IY=IYM,IYP
                IF(IY.GE.IY0) FY=1./ISYP/SQRT2
                IF(IY.LT.IY0) FY=1./ISYM/SQRT2
                FX=1./ISXM/SQRT2
                DO 200 IX=IXM,IX0
                        ISUB=ISI*IFIX(0.5+FIA
     1                    *EXP(-((IX-IX0)*FX)**2-((IY-IY0)*FY)**2))
                        IZ(IX,IY)=IZ(IX,IY)-ISUB
200                 CONTINUE
                FX=1./ISXP/SQRT2
                IX0P1=IX0+1
                DO 400 IX=IX0P1,IXP
                        IZ(IX,IY)=IZ(IX,IY)-ISI*IFIX(0.5+FIA
     1                    *EXP(-((IX-IX0)*FX)**2-((IY-IY0)*FY)**2))
400                 CONTINUE
500     CONTINUE
        RETURN
        END
```

We claim:

1. A method of quantitating spatially-integrated intensities of individual spots contained in a multiple spot image defined by a discrete pixel-by-pixel representation of the intensity of the spots comprising the steps of:
   (a) searching the image for the pixel representing the greatest intensity deviation in each of two opposite senses from a reference intensity level,
   (b) constructing a mathematical three-dimensional model, in a sense corresponding to the sense of the maximum pixel found, of the spot containing such pixel, one of the dimensions being related to spot intensity,
   (c) compensating the image by subtracting the mathematical model therefrom leaving possible overcompensated regions in the image which in turn can give rise to additional pixels that will subsequently be detected in step (a),
   (f) quantitating the spot from the model by determining the volume of the model by multiplying the model's dimensions together, and
   (g) repeating steps (a) through (d) for successive pixels each having a lower intensity deviation from the reference level until the image is of substantially constant intensity.

2. The method set forth in claim 1 wherein the mathematical model is a Gaussian model.

3. The method set forth in claim 1 wherein the model step (b) is formed by least squares curve fitting.

4. The method set forth in claim 1 wherein the model of step (b) is defined by searching the image in four orthogonal directions from the greatest deviation pixel to ascertain the length and width of the spot along each direction.

5. The method set forth in claim 4 wherein the model of step (b) is formed to be an asymmetric function of position relative to the greatest deviation pixel.

6. The method set forth in claim 5 wherein the model of step (b) is formed by least-squares curve fitting.

7. The method set forth in claim 5 wherein models formed in step (b) of nearby pixels are combined to form composite models of each individual spot.

8. The method set forth in claim 7 which includes the additional step of determining the extent of the composite model by combining component model moments of inertia according to the parallel-axis theorem.

9. The method set forth in claim 4 wherein models formed in step (b) of nearby pixels are combined to form composite models of each individual spot.

10. The method set forth in claim 1 wherein models formed in step (b) of nearby pixels are combined to form composite models of each individual spot.

11. In a system for quantitating individual spots contained in a multiple spot image defined by a discrete pixel-by-pixel representation of the intensity of the spots, the system including a memory for storing the pixels, means for determining that pixel representing the greatest intensity deviation from a reference intensity level, and means for constructing a mathematical three-dimension model of the spot containg such pixel, one of the dimensions corresponding to spot intensity, the improvement which includes:

means includes in the determining means for determining that pixel representing the greatest intensity deviation in each of two opposite senses from the reference intensity level, means included in the constructing means for constructing the model in a sense corresponding to the sense of the maximum pixel found, means for compensating the image by subtracting the mathematical model therefrom leaving possible overcompensated regions in the stored image which in turn can give rise to additional pixels, and means for quantitating the spot from the model by determining the volume of the model by multiplying the model diemensions together.

\* \* \* \* \*